United States Patent
Becher et al.

(10) Patent No.: US 6,908,882 B1
(45) Date of Patent: Jun. 21, 2005

(54) ENHANCED METHOD OF KILLING WEEDS WITH GLYPHOSATE HERBICIDE

(75) Inventors: David Z. Becher, Creve Coeur, MO (US); Al S. Wideman, St. Louis, MO (US); James C. Forbes, Glenview, IL (US)

(73) Assignee: Monsanto Company, St. Louis, MO (US)

( * ) Notice: Subject to any disclaimer, the term of this patent is extended or adjusted under 35 U.S.C. 154(b) by 495 days.

(21) Appl. No.: 09/652,771

(22) Filed: Aug. 31, 2000

Related U.S. Application Data

(60) Provisional application No. 60/153,140, filed on Sep. 9, 1999.

(51) Int. Cl.$^7$ ............................ A01N 3/02; A01N 57/00
(52) U.S. Cl. ...................................... 504/116.1; 504/206
(58) Field of Search ............................... 504/116.1, 206

(56) References Cited

U.S. PATENT DOCUMENTS

| | | | | |
|---|---|---|---|---|
| 5,710,103 A | * | 1/1998 | Magin et al. | ................ 504/206 |
| 5,985,798 A | * | 11/1999 | Crudden | ..................... 504/206 |

FOREIGN PATENT DOCUMENTS

| | | | |
|---|---|---|---|
| WO | WO 95/16352 | | 6/1995 |
| WO | WO 97/03560 | | 2/1997 |
| WO | 9921423 | * | 5/1999 |
| WO | WO 99/62338 | | 12/1999 |

* cited by examiner

Primary Examiner—Alton N. Pryor
(74) Attorney, Agent, or Firm—Senniger Powers; Joseph A. Schaper; James C. Forbes

(57) ABSTRACT

A method is provided of enhancing the herbicidal activity of a glyphosate herbicide, comprising adding to the glyphosate herbicide a mixture of a first surfactant and a second surfactant at a weight ratio of total surfactant to glyphosate of about 1:30 to about 2:1, wherein the first surfactant has a chemical structure comprising a cationic or protonatable amino group and a $C_{8-24}$ linear or branched, saturated or unsaturated hydrocarbyl group, and the second surfactant has the formula

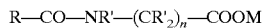

where R is a $C_{7-23}$ linear or branched, saturated or unsaturated hydrocarbyl group, n is 1 to 4, M is hydrogen or a cationic counterion, and R' groups are each independently hydrogen, $C_{1-4}$ alkyl or a group —$(CH_2)_m$—COOM where m is 1 to 4 and M is as defined immediately above, with the proviso that no more than one R' group is such a group —$(CH_2)_m$—COOM; the weight ratio of the first to the second surfactant being about 1:10 to about 10:1.

Also provided is a herbicidal composition prepared according to the above method. The first and second surfactants exhibit a synergistic interaction in enhancing herbicidal activity of the glyphosate herbicide.

32 Claims, No Drawings

ENHANCED METHOD OF KILLING WEEDS WITH GLYPHOSATE HERBICIDE

CROSS-REFERENCE TO RELATED APPLICATIONS

This application claims the benefit of U.S. Provisional Application No. 60/153,140 filed Sep. 9, 1999.

FIELD OF THE INVENTION

The present invention relates to a method of killing or controlling the growth of undesirable plants using a glyphosate herbicide. By exploiting a newly discovered synergistic interaction between two classes of surfactant applied together with the glyphosate, surprisingly enhanced herbicidal effectiveness is obtained by this method.

BACKGROUND OF THE INVENTION

Glyphosate herbicides include N-phosphonomethylglycine, sometimes referred to as "glyphosate acid", salts and esters thereof, and other compounds which when applied to plants release or otherwise provide glyphosate ions. Long known as useful herbicides, glyphosate herbicides are generally applied in aqueous solution or dispersion, most commonly by spraying, to foliage of plants to be killed or controlled. Plants growing where they are not desired are herein referred to for convenience as "weeds", but it should be recognized that glyphosate herbicides are frequently used for killing or controlling plants not normally thought of as weeds, such as volunteer plants of a crop species growing in a crop of another species, or pasture plants that have outlived their period of maximum productivity.

In most commercial glyphosate herbicide formulations, the glyphosate is present as a water-soluble salt. Herbicidal salts of glyphosate are disclosed, for example, in U.S. Pat. No. 3,799,758 to Franz, U.S. Pat. No. 3,853,530 to Franz, U.S. Pat. No. 4,140,513 to Prill, U.S. Pat. No. 4,315,765 to Large, U.S. Pat. No. 4,405,531 to Franz, U.S. Pat. No. 4,481,026 to Prisbylla and U.S. Pat. No. 4,507,250 to Bakel. Glyphosate salts disclosed include alkali metal, for example sodium and potassium, salts; ammonium salt; and numerous salts having an ammonium, sulfonium or sulfoxonium cation substituted with 1—3 organic groups containing in total 1–6 carbon atoms, for example dimethylammonium, isopropylammonium, ethanolammonium and trimethylsulfonium salts.

Commercial formulations of glyphosate salts include, for example, Roundup®, Accord®, Roundup® Ultra and Roundup® Xtra herbicides of Monsanto Company, which contain the isopropylammonium salt, Roundup® Dry and Rival® herbicides of Monsanto Company, which contain the ammonium salt, Roundup® Geoforce herbicide of Monsanto Company, which contains the sodium salt, and Touchdown® herbicide of Zeneca, which contains the trimethylsulfonium salt.

Glyphosate herbicides are in most cases formulated by the manufacturer, and/or mixed by the end user, with one or more surfactants. Surfactants assist in retention of droplets of the applied spray on the foliage of treated plants, adhesion of the spray droplets to the foliar surface and penetration of the water-soluble pesticide through the hydrophobic cuticle that covers the foliar surface, by these means and possibly in other ways enhancing herbicidal activity of the glyphosate. An extensive study by Wyrill & Burnside, *Weed Science* 25, 275–287, 1977 led to a conclusion that "an effective surfactant is a critical component of any glyphosate spray mixture", but noted great variation among surfactant types in the degree of enhancement of herbicidal activity afforded. In general, cationic surfactants gave the greatest degree of enhancement. The authors also remarked that the effectiveness of combinations of surfactants was generally unpredictable, and warned against the "indiscriminate mixing of surfactants" in glyphosate spray compositions.

Among cationic surfactants known to be effective in enhancing activity of glyphosate herbicides are tertiary alkylamines, polyoxyethylene tertiary alkylamines, quaternary alkylammonium salts and polyoxyethylene quaternary alkylammonium salts. The term "alkyl" in the present context is used conventionally to refer to straight and branched chain, saturated and unsaturated aliphatic hydrocarbyl groups having about 8 to about 24 carbon atoms. Also effective are etheramine surfactants, in which the carbon chain of the hydrocarbyl group is interrupted by one or more ether linkages. Many other variants of such amine-based surfactants are also known, including polyoxypropylene quaternary ammonium salts, diamines and amphoteric types such as alkylamine oxides, alkylbetaines, etc., all having in common, like the cationic surfactants mentioned above, the possession of a cationic or protonatable amino group. Glyphosate herbicide compositions comprising one or more amine-based surfactants are disclosed illustratively in U.S. Pat. No. 5,118,444 to Nguyen, U.S. Pat. No. 5,317,003 to Kassebaum & Berk, U.S. Pat. No. 5,668,085 to Forbes et al., U.S. Pat. No. 5,750,468 to Wright et al., U.S. Pat. No. 5,821,195 to Sandbrink et al., Australian Patent No. 595406, and International Publication Nos. WO 95/33379, WO 97/05779, WO 97/31890, WO 97/36494, WO 98/24313, WO 98/53680, WO 99/00012 and WO 99/05914.

Anionic surfactants are in general weak potentiators of glyphosate herbicidal activity. However, International Publication No. WO 99/21423 discloses compositions comprising a glyphosate herbicide and an anionic N-acyl sarcosine or sarcosinate surfactant which are said to "maintain [the] herbicidal efficacy" of a commercial glyphosate herbicidal formulation. An example of such a composition, applied at 100 g glyphosate acid equivalent (a.e.) per acre (approximately 240 g a.e./ha), is reported therein to give 65% "overall kill" of mixed broadleaf weeds and grasses 21 days after application, by comparison with 62% "overall kill" achieved with the commercial glyphosate formulation Roundup® applied at the same rate. The weight ratio of N-alkyl sarcosinate to glyphosate a.e. in the disclosed composition is calculated to be approximately 1:16. At this very low surfactant to glyphosate ratio the composition had low eye irritancy potential by comparison with Roundup® herbicide which has a much higher surfactant concentration. Unfortunately no data are provided on the degree of "overall kill" provided in the absence of surfactant; without such data it is not possible to determine whether or not the N-alkyl sarcosinate was effective in enhancing herbicidal activity of glyphosate under the conditions of the test reported.

Combinations of cationic and certain anionic surfactants have previously been disclosed to provide, in combination with a glyphosate herbicide, formulations of low eye irritancy. For example, U.S. Pat. No. 5,683,958 to Berger & Jimenez discloses compositions comprising a glyphosate herbicide, a polyoxyethylene alkylamine surfactant and an alkyl sulfate, polyoxyethylene alkyl or alkylphenol sulfate, alkyl phosphate, polyoxyethylene alkyl or alkylphenol phosphate or polyoxyethylene alkyl or alkylphenol carboxylate surfactant; and U.S. Pat. No. 5,389,598 to Berk & Kassebaum discloses compositions comprising a glyphosate herbicide, a polyoxyethylene alkylamine surfactant and an alkyl mono- or dicarboxylic acid, for example a fatty acid, as having low eye irritancy. However, such compositions have not been disclosed to have herbicidal efficacy that is unexpectedly enhanced by comparison with otherwise similar compositions having only one of the two surfactant components.

SUMMARY OF THE INVENTION

It has now been found that addition to a glyphosate herbicide of a composition having at least two surfactants, one of which has a cationic or protonatable amino group and the other of which is an anionic N-acyl derivative of an amino acid or a salt thereof, unexpectedly provides herbicidal activity that is synergistically greater than that provided by either one of these surfactants alone at an equal weight ratio of total surfactant to glyphosate.

Accordingly there is now provided a method of enhancing the herbicidal activity of a glyphosate herbicide, this method comprising adding to the glyphosate herbicide a mixture of a first surfactant and a second surfactant at a weight ratio of total surfactant to glyphosate of about 1:30 to about 2:1, wherein the first surfactant has a chemical structure comprising a cationic or protonatable amino group and a $C_{8-24}$ linear or branched, saturated or unsaturated hydrocarbyl group, and the second surfactant has the formula

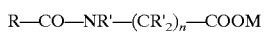

R—CO—NR'—(CR'$_2$)$_n$—COOM where R is a $C_{7-23}$ linear or branched, saturated or unsaturated hydrocarbyl group, n is 1 to 4, M is hydrogen or a cationic counterion, and R' groups are each independently hydrogen, $C_{1-4}$ alkyl or a group —(CH$_2$)$_m$—COOM where m is 1 to 4 and M is as defined immediately above, with the proviso that no more than one R' group is such a group —(CH$_2$)$_m$—COOM; the weight ratio of the first to the second surfactant being about 1:10 to about 10:1.

An embodiment of the invention is a composition formed by admixing a glyphosate herbicide, a first surfactant and a second surfactant in accordance with the method just described. Such a composition can be a liquid that further comprises about 30% to about 99.9% by weight of a solvent or dispersion medium, typically water, for the glyphosate herbicide, the first surfactant and the second surfactant. A liquid aqueous composition of the invention can be, for example, a dilute aqueous plant treatment composition having a glyphosate a.e. content of about 0.1% to about 10% by weight, or an aqueous concentrate composition having a glyphosate a.e. content of about 10% to about 50% by weight that can be further diluted with water to form such a plant treatment composition. Alternatively, the composition can be a dry solid that further comprises 0 to about 90% by weight of an inert solid filler and that can be dissolved or dispersed in water to form such a plant treatment composition.

A further embodiment of the invention is a method of killing or controlling weeds comprising application to foliage of the weeds a dilute aqueous plant treatment composition as described herein.

DETAILED DESCRIPTION OF THE INVENTION

The surprising discovery underlying the present invention is that the first and second surfactants interact synergistically in enhancing the herbicidal activity of a co-applied glyphosate herbicide. A synergistic interaction between two surfactants is typically defined in the relevant art as one wherein, at a given weight ratio of total surfactant to active ingredient (in this case glyphosate a.e.), the herbicidal activity observed with a mixture of the two surfactants is greater than an expected level of activity intermediate between that observed with each of the two surfactants applied in the absence of the other surfactant. For the present invention, a more demanding standard was set, viz., that the herbicidal activity observed with a mixture of the two surfactants, at a given weight ratio of total surfactant to active ingredient, should be greater than that observed by either one of the surfactants applied in the absence of the other surfactant. Typically one surfactant is more effective than the other when present as the sole surfactant; thus to meet the standard of synergism set for the present invention, the effectiveness of a mixture of the two surfactants must exceed that of the more effective surfactant alone at the same total surfactant to glyphosate a.e. ratio.

For illustration, consider two hypothetical compositions each containing 10 parts by weight glyphosate a.e. and 2 parts by weight surfactant, applied side by side to weeds at a glyphosate application rate of 500 g a.e./ha. The only difference between the compositions is the nature of the surfactant, in one composition being surfactant X and in the other surfactant Y. Suppose that the composition having surfactant X gives 80% control and the composition having surfactant Y gives 60% control. A third hypothetical composition containing 10 parts by weight glyphosate a.e., 1 part by weight surfactant X and 1 part by weight surfactant Y would be expected on this basis to give about 70% control; greater than 70% control would ordinarily be considered evidence of synergism. However, to meet the standard set for the present invention, this third composition has to give greater than 80% control, the level of control achieved with surfactant X as sole surfactant.

The first surfactant according to the present invention has a chemical structure comprising at least one cationic or protonatable amino group. Presently preferred such surfactants include tertiary alkylamines and alkyletheramines, polyoxyethylene tertiary alkylamines and alkyletheramines, quaternary ammonium surfactants, pyridine and imidazoline surfactants, polyoxyethylene alkylamine and alkyletheramine oxides, alkylbetaines, alkyl diamines and polyoxyethylene alkyl diamines.

Tertiary alkylamine and alkyletheramine surfactants useful in practice of the invention include those having the chemical formula

where $R^1$ is a $C_{8-24}$, preferably a $C_{12-18}$, straight or branched chain, saturated or unsaturated hydrocarbyl group, optionally interrupted by one or more ether linkages, and $R^2$ and $R^3$ are (a) independently $C_{1-4}$ alkyl, preferably methyl, groups, or (b) polyoxyalkylene chains having in total 2 to about 100 $C_{2-4}$ alkylene oxide units, preferably ethylene oxide units. Preferred polyoxyethylene alkyletheramines are those wherein $R^1$ is a group R—(O—A)$_x$— where R is $C_{8-15}$ alkyl, O—A groups are independently oxyethylene, oxyisopropylene or oxy-n-propylene units and x is 1 to 5.

Quaternary ammonium surfactants useful in practice of the invention include those having the chemical formula

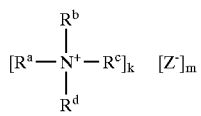

where $Z^-$ is a suitable anion such as chloride, bromide, iodide, acetate, salicylate, sulfate or phosphate; k and m are integers such that the positive electrical charges on cations balance the negative electrical charges on anions; and options for $R^a$, $R^b$, $R^c$ and $R^d$ include, without limitation, the following:

(i) $R^a$ is a benzyl or $C_{8-24}$, preferably a $C_{12-18}$, straight or branched chain, saturated or unsaturated hydrocarbyl group, optionally interrupted by one or more ether linkages, and $R^b$, $R^c$ and $R^d$ are independently $C_{1-4}$ allyl, preferably methyl, groups;

(ii) $R^a$ and $R^b$ are independently $C_{8-24}$, preferably $C_{12-18}$, straight or branched chain, saturated or unsaturated hydrocarbyl groups, each optionally interrupted by one or more ether linkages, and $R^c$ and $R^d$ are independently $C_{1-4}$ alkyl, preferably methyl, groups;

(iii) $R^a$ is a $C_{8-24}$, preferably a $C_{12-18}$, straight or branched chain, saturated or unsaturated hydrocarbyl group, optionally interrupted by one or more ether linkages, $R^b$ is a polyoxyalkylene chain having about 2 to about 100, preferably about 2 to about 25, $C_{2-4}$ alkylene oxide units, preferably ethylene oxide units, and $R^c$ and $R^d$ are independently $C_{1-4}$ alkyl, preferably methyl, groups;

(iv) $R^a$ is a $C_{8-24}$, preferably a $C_{12-18}$, straight or branched chain, saturated or unsaturated hydrocarbyl group, optionally interrupted by one or more ether linkages, $R^b$ and $R^c$ are polyoxyalkylene chains having in total 2 to about 100, preferably 2 to about 25, $C_{2-4}$ alkylene oxide units, preferably ethylene oxide units, and $R^d$ is a $C_{1-4}$ alkyl, preferably a methyl, group; or (v) $R^a$ is a polyoxyalkylene chain having about 2 to about 100, preferably about 2 to about 25, $C_{2-4}$ alkylene oxide wilts in which $C_{3-4}$ alkylene oxide units, preferably propylene oxide units, predominate, and $R^b$, $R^c$ and $R^d$ are independently $C_{1-4}$ alkyl, preferably methyl or ethyl, groups. Particularly preferred quaternary ammonium surfactants of this type are those disclosed in U.S. Pat. No. 5,464,807.

Illustrative polyoxyethylene quaternary alkyletherammonium surfactants are those of options (i) to (iv) immediately above wherein the recited $C_{8-24}$ hydrocarbyl group is interrupted by one or more ether linkages and can be represented as a group $R—(O—A)_x—$ where R is $C_{8-15}$ alkyl, O—A groups are independently oxyethylene, oxyisopropylene or oxy-n-propylene units and x is 1 to 5.

The second surfactant according to the present invention has the formula

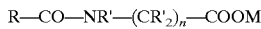

where R is a $C_{7-23}$ linear or branched, saturated or unsaturated hydrocarbyl group, n is 1 to 4, M is hydrogen or a cationic counterion, and R' groups are each independently hydrogen, $C_{1-4}$ alkyl or a group 13 $(CH_2)_m$—COOM where m is 1 to 4 and M is as defined immediately above, with the proviso that no more than one R' group is such a group —$(CH_2)_m$—COOM.

It will be seen from the formula for the second surfactant that the hydrophobic group R—C(O)— is a $C_{8-24}$ acyl moiety. Preferably this acyl moiety has about 12 to about 18 carbon atoms. Preferably the acyl moiety is linear and derived from a saturated or unsaturated fatty acid; typically a preparation of the second surfactant consists of a mixture of compounds having a variety of acyl moieties, as results from the use of fatty acids from natural oils such as coconut oil, palm oil, soybean oil, tallow, etc. For example, the acyl moiety can be represented as "cocoyl", which means that a variety of acyl moieties are present in the surfactant, approximately in the proportion in which the parent fatty acids are present in coconut oil (predominantly $C_{12}$ and $C_{14}$ saturated acyl moieties in this instance). Alternatively, the acyl moiety can be essentially homogeneous, e.g., lauroyl, myristoyl, palmitoyl, linoleoyl, linolenoyl, stearoyl, oleoyl, etc.

In the formula for the second surfactant, R' groups are preferably selected from hydrogen and methyl groups, except that one R' group, preferably an R' group attached to a carbon rather than a nitrogen atom, can optionally be a group —$(CH_2)_m$—COOM as indicated above.

Each M in the formula for the second surfactant is independently selected from hydrogen or a cationic counterion. Typically the second surfactant is added in the form of an acid or a salt having a low molecular weight cation such as an alkali metal, e.g., sodium or potassium, cation, an ammonium cation or a $C_{1-4}$ organic ammonium, e.g., dimethylammonium, isopropylammonium or ethanolammonium, cation; in the case of a second surfactant having two —COOM groups, the salt can be a mono- or a di-salt with such a low molecular weight cation. Once in a composition together with the first surfactant and glyphosate, the cationic counterion M can also include the first surfactant itself and/or any cationic counterion introduced with the glyphosate.

Preferably the second surfactant is an N-acyl derivative of an α- or β-amino acid, in which n is 1 or 2 respectively; more preferably n is 1. In one embodiment the second surfactant is an N-acyl derivative of the α-amino acid sarcosine, having the formula

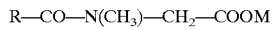

wherein R and M are as defined herein. In another embodiment the second surfactant is an N-acyl derivative of the α-amino acid glutamic acid, having the formula

wherein R and M are as defined herein. Examples of commercially available N-acyl derivatives of sarcosine and glutamic acid are cocoyl glutamic acid, available for example as Amisoft™ of Ajinomoto, cocoyl sarcosine, available for example as Crodasinic™ C of Croda, Hamposyl™ C of Hampshire and Vanseal™ CS of Vanderbilt, lauroyl sarcosine, available for example as Hamposyl™ L of Hampshire, and oleoyl sarcosine, available for example as Hamposyl™ O of Hampshire.

Other α-amino acids, N-acyl derivatives of which can be useful, illustratively include alanine, aspartic acid, glycine, isoleucine, leucine and valine.

In a method or composition of the invention, the first and second surfactants are present in a weight ratio of about 1:10 to about 10:1. Suitably the weight ratio of the first to the second surfactant is about 1:5 to about 5:1. The weight ratio of total surfactant (first and second surfactants together) to glyphosate a.e. is about 1:30 to about 2:1, preferably about 1:10 to about 1:1. Below a surfactant to glyphosate a.e. weight ratio of about 1:10 there is unlikely to be a sufficient amount of surfactant to give reliable kill or control of weeds; above a ratio of about 1:1 the herbicidal treatment is unlikely to be economically efficient, although it may be highly effective. Especially where it is desired to prepare a concentrate composition comprising both glyphosate and the mixture of first and second surfactants, a high surfactant to glyphosate a.e. ratio renders it impossible to provide a composition having a very high loading of glyphosate. Particularly suitable weight ratios of total surfactant to glyphosate a.e. are in the range from about 1:6 to about 1:2.

Glyphosate can be present in the form of glyphosate acid or any derivative thereof that exhibits glyphosate herbicidal activity. Preferably the glyphosate is present in the form of one or more water-soluble salt(s), more preferably one or more water-soluble salt(s) wherein the counterions are monovalent. Glyphosate monosalts, disalts and mixtures thereof are equally useful. Especially suitable counterions illustratively include sodium, potassium, ammonium, organic ammonium and organic sulfonium cations, wherein organic ammonium or organic sulfonium cations have from 1 to about 16 carbon atoms. Preferred organic ammonium cations are dimethylammonium, monoethanolammonium, n-propylammonium and isopropylammonium cations. Preferred organic sulfonium cations are trimethylsulfonium cations.

A composition of the invention can be a liquid plant treatment composition or a liquid concentrate composition that further comprises about 30% to about 99.9% by weight of a solvent or dispersion medium, typically water, for the glyphosate herbicide, the first surfactant and the second surfactant. A dilute aqueous plant treatment composition of the invention typically has a glyphosate a.e. content of about 0.1% to about 10%, preferably about 0.2% to about 2%, by weight. An aqueous concentrate composition of the invention typically has a glyphosate a.e. content of about 10% to about 50%, preferably about 30% to about 45%, by weight. Expressed as weight/volume concentration, an aqueous concentrate composition of the invention typically has a glyphosate loading of about 100 to about 600 g a.e./l, preferably about 180 to about 540 g a.e/l.

Aqueous concentrate compositions of the invention include formulation types known in the art as soluble concentrates (SL), oil-in-water emulsions (EW), water-based suspension concentrates (SC) and suspoemulsions (SE). Aqueous concentrate compositions consisting essentially of water, a water-soluble glyphosate salt, a first surfactant and a second surfactant in accordance with the invention are typically soluble concentrates.

Alternatively, a composition of the invention can be a dry solid formulation such as a powder, granules, pellets or tablets. Such a dry solid formulation is generally water-soluble or water-dispersible. In one embodiment the dry solid further comprises up to 90% by weight of an inert solid filler which may be water-soluble, e.g., an inorganic salt such as ammonium sulfate, or water-insoluble, e.g., finely powdered silica. In a preferred embodiment the dry solid is water-soluble and has substantially no inert filler. Dry water-soluble or water-dispersible compositions of the invention typically have a glyphosate a.e. content of about 5% to about 80%, preferably about 50% to about 75%, by weight.

Compositions of the invention can optionally contain one or more additional herbicidal active ingredients other than glyphosate. Inert or excipient ingredients other than water, a solid filler, the first surfactant and the second surfactant can also optionally be included in a composition of the invention. Such ingredients include surfactants other than those meeting the description herein of first or second surfactant, for example nonionic surfactants such as polyoxyethylene alkylethers, polyoxyethylene alkylphenylethers, sorbitan esters and alkyl polyglycosides. Other optional excipient ingredients include oils, solvents, stabilizing agents, antifreeze agents and pour point depressants such as glycols, dyes, inorganic salts such as ammonium sulfate, fertilizers, foam moderating agents, thickeners, drift control agents, etc.

A method of killing or controlling weeds according to the invention comprises application to foliage of the weeds a dilute aqueous plant treatment composition as described herein.

The selection of application rates for a composition of the invention that are herbicidally effective is within the skill of the ordinary agricultural scientist. Those of skill in the art will likewise recognize that individual plant conditions, weather and growing conditions, as well as the specific composition selected, will influence the degree of herbicidal effectiveness achieved in practicing this invention. Much information is known about appropriate application rates for glyphosate herbicides. Over two decades of glyphosate use and published studies relating to such use have provided abundant information from which a weed control practitioner can select glyphosate application rates that are herbicidally effective on particular species at particular growth stages in particular environmental conditions.

Herbicidal compositions of glyphosate or derivatives thereof are used to control a very wide variety of plants worldwide. Glyphosate compositions of the invention can be applied to a plant in a herbicidally effective amount, and can effectively control one or more plant species of one or more of the following genera without restriction: *Abutilon, Amaranthus, Artemisia, Asclepias, Avena, Axonopus, Borreria, Brachiaria, Brassica, Bromus, Chenopodium, Cirsium, Commelina, Convolvulus, Cynodon, Cyperus, Digitaria, Echinochloa, Eleusine, Elymus, Equisetum, Erodium, Helianthus, Imperata, Ipomoea, Kochia, Lolium, Malva, Oryza, Ottochloa, Panicum, Paspalum, Phalaris, Phragmites, Polygonum, Portulaca, Pteridium, Pueraria, Rubus, Salsola, Setaria, Sida, Sinapis, Sorghum, Triticum, Typha, Ulex, Xanthium* and *Zea*.

Particularly important annual broadleaf species for which glyphosate compositions are used are exemplified without limitation by the following: velvetleaf (*Abutilon theophrasti*), pigweed (*Amaranthus* spp.), buttonweed (*Borreria* spp.), oilseed rape, canola, indian mustard, etc. (*Brassica* spp.), commelina (*Commelina* spp.), filaree (*Erodium* spp.), sunflower (*Helianthus* spp.), morningglory (*Ipomoea* spp.), kochia (*Kochia scoparia*), mallow (*Malva* spp.), wild buckwheat, smartweed, etc. (*Polygonum* spp.), purslane (*Portulaca* spp.), russian thistle (*Salsola* spp.), sida (*Sida* spp.), wild mustard (*Sinapis arvensis*) and cocklebur (*Xanthium* spp.)

Particularly important annual narrowleaf species for which glyphosate compositions are used are exemplified without limitation by the following: wild oat (*Avena fatua*), carpetgrass (*Axonopus* spp.), downy brome (*Bromus tectorum*), crabgrass (*Digitaria* spp.), barnyardgrass (*Echinochloa crus-galli*), goosegrass (*Eleusine indica*), annual ryegrass (*Lolium multiflorum*), rice (*Oryza sativa*), ottochloa (*Ottochloa nodosa*), bahiagrass (*Paspalum notatum*), canarygrass (*Phalaris* spp.), foxtail (*Setaria* spp.), wheat (*Triticum aestivum*) and corn (*Zea mays*).

Particularly important perennial broadleaf species for which glyphosate compositions are used are exemplified without limitation by the following: mugwort (*Artemisia* spp.), milkweed (*Asclepias* spp.), canada thistle (*Cirsium arvense*), field bindweed (*Convolvulus arvensis*) and kudzu (*Pueraria* spp.).

Particularly important perennial narrowleaf species for which glyphosate compositions are used are exemplified without limitation by the following: brachiaria (*Brachiaria* spp.), bermudagrass (*Cynodon dactylon*), yellow nutsedge (*Cyperus esculentus*), purple nutsedge (*C. rotundus*), quackgrass (*Elymus repens*), lalang (*Imperata cylindrica*), perennial ryegrass (*Lolium perenne*), guineagrass (*Panicum maximum*), dallisgrass (*Paspalum dilatatum*), reed (*Phragmites* spp.), johnsongrass (*Sorghum halepense*) and cattail (*Typha* spp.).

Other particularly important perennial species for which glyphosate compositions are used are exemplified without limitation by the following: horsetail (*Equisetum* spp.), bracken (*Pteridium aquilinum*), blackberry (*Rubus* spp.) and gorse (*Ulex europaeus*).

Thus, plant treatment compositions of the present invention, and a method for treating plants with such compositions, can be useful on any of the above species. In a particular contemplated method, a plant treatment composition of the invention comprising glyphosate in the form of one or more water-soluble salt(s) thereof is applied to foliage of crop plants genetically transformed to tolerate glyphosate, and simultaneously to foliage of weeds or undesired plants growing in close proximity to such crop plants. This method results in control of the weeds or undesired plants while leaving the crop plants substantially unharmed. Crop plants genetically transformed to tolerate glyphosate include those whose seeds are sold by Monsanto or under license from Monsanto bearing the Roundup Ready® trademark. These include varieties of cotton, soybean, canola, sugar beet and corn.

Application of plant treatment compositions to foliage of plants is preferably accomplished by spraying, using any conventional means for spraying liquids, such as spray nozzles or spinning-disk atomizers. Compositions of the present invention can be used in precision farming techniques, in which apparatus is employed to vary the amount of exogenous chemical substance applied to different parts of a field, depending on variables such as the particular plant species present, plant growth stage, soil moisture status, etc. In one embodiment of such techniques, a global positioning system operated with the spraying apparatus can be used to control application of the composition in desired amounts to different parts of a field.

A plant treatment composition is preferably dilute enough to be readily sprayed using standard agricultural spray equipment. Suitable spray volumes for the present invention vary depending upon a number of factors, including the plant species involved. Useful spray volumes for applying an aqueous plant treatment composition to a field can range from about 25 to about 1000 l/ha, preferably about 50 to about 300 l/ha.

EXAMPLES

Compositions of Examples 1 and 2 hereinbelow were prepared by mixing the following ingredients together with water in the proportions shown:

MON 0139: a concentrated aqueous solution of glyphosate isopropylammonium salt having an assay of 46% glyphosate a.e.;

polyoxyethylene (15) tallowamine;

isopropylammonium cocoyl sarcosinate (prepared in situ by adding cocoyl sarcosine, e.g., Hamposyl™ C, and isopropylamine in an approximately 1:1 mole ratio).

As described more fully below, compositions A–E each contained about 18% glyphosate a.e. by weight, equivalent to a glyphosate loading of about 200 g a.e./l. Each further contained a total of about 4.5% surfactant, thus having a surfactant to glyphosate a.e. ratio by weight of about 1:4; in computing the amount of surfactant the weight of cocoyl sarcosine was considered, excluding the weight of the isopropylammonium counterion. Composition A contained 4.5% by weight of cocoyl sarcosine as sole surfactant. Composition B contained 4.5% by weight of polyoxyethylene (15) tallowamine as sole surfactant. Compositions C–E contained 4.5% by weight of a mixture of polyoxyethylene (15) tallowamine and cocoyl sarcosine, in a ratio by weight of about 1:3, 1:1 and 3:1 respectively.

The ingredients (all percentages are by weight) of Compositions A–E were as follows:

| | A | B | C | D | E |
|---|---|---|---|---|---|
| MON 0139 | 39.63% | 39.97% | 39.72% | 39.80% | 39.88% |
| polyoxyethylene (15) tallowamine | | 4.49% | 1.12% | 2.25% | 3.37% |
| cocoyl sarcosine | 4.51% | | 3.38% | 2.25% | 1.13% |
| isopropylamine | 2.76% | | 2.07% | 1.38% | 0.69% |
| Water | 53.10% | 55.54% | 53.71% | 54.32% | 54.93% |

In Examples 1 and 2 below, compositions A–E were subjected to greenhouse testing for herbicidal effectiveness by the following procedure.

Seeds of the plant species indicated were planted in 85 mm square pots in a soil mix which was previously steam sterilized and prefertilized with a 14-14-14 NPK slow release fertilizer at a rate of 3.6 kg/m$^3$. The pots were placed in a greenhouse with sub-irrigation. About one week after emergence, seedlings were thinned as needed, including removal of any unhealthy or abnormal plants, to create a uniform series of test pots.

The plants were maintained for the duration of the test in the greenhouse where they received a minimum of 14 hours of light per day. If natural light was insufficient to achieve the daily requirement, artificial light with an intensity of approximately 475 microeinsteins was used to make up the difference. Exposure temperatures were not precisely controlled but averaged about 27° C. during the day and about 18° C. during the night. Plants were sub-irrigated throughout the test to ensure adequate soil moisture.levels. Relative humidity was maintained at about 50% for the duration of the test.

Pots were assigned to different treatments in a fully randomized experimental design with 6 replications. A set of pots was left untreated as a reference against which effects of the treatments could later be evaluated.

Application of glyphosate compositions to foliage was made by spraying with a track sprayer fitted with a TeeJet™ 9501 E nozzle calibrated to deliver a spray volume of 93 l/ha at a pressure of 165 kPa. After treatment, pots were returned to the greenhouse until ready for evaluation.

Treatments were made using dilute aqueous compositions, prepared by dilution with water of the preformulated Compositions A–E. All comparisons were made at equal glyphosate a.e. rates. The required degree of dilution for a glyphosate concentrate composition to make a plant treatment composition is calculated from the equation $$A = RS/VC$$

where A is the volume in milliliters (ml) of the glyphosate composition to be added to the plant treatment composition being prepared, R is the desired glyphosate rate in grams of acid equivalent per hectare (g a.e./ha), S is the total volume in milliliters (ml) of plant treatment composition being prepared, V is the application rate in liters per hectare (l/ha) of plant treatment composition, conventionally referred to as "spray volume", and C is the concentration of glyphosate in grams of acid equivalent per liter (g a.e./l) in the glyphosate composition.

For evaluation of herbicidal effectiveness, all plants in the test were examined by a single practiced technician, who recorded percent inhibition, a visual measurement of the effectiveness of each treatment by comparison with untreated plants. Inhibition of 0% indicates no effect, and inhibition of 100% indicates that all of the plants are completely dead. Inhibition of 85% or more is in most cases considered acceptable for normal herbicidal use; however in greenhouse tests such as the one described in Examples 1 and 2 it is normal to apply compositions at rates which are expected to give less than 85% inhibition, as this makes it easier to discriminate among compositions having different levels of effectiveness.

Example 1

Compositions A–E were tested on velvetleaf (*Abutilon theophrasti*, ABUTH) and Japanese millet, a form of barnyardgrass (*Echinochloa crus-galli*, ECHCF). Plants of both species were sprayed 17 days after planting. Evaluation of herbicidal effectiveness was conducted 17 days after treatment (DAT). Results are shown in the following table.

| Composition | Glyphosate rate g a.e./ha | % Inhibition ABUTH | ECHCF |
|---|---|---|---|
| A | 100 | 0 | 2 |
| (2nd surfactant only) | 200 | 43 | 40 |
| | 300 | 60 | 40 |
| | 400 | 73 | 55 |
| B | 100 | 0 | 13 |
| (1st surfactant only) | 200 | 57 | 55 |
| | 300 | 62 | 75 |
| | 400 | 70 | 79 |
| C | 100 | 36 | 45 |
| (1st + 2nd surfactant, 1:3 ratio) | 200 | 71 | 65 |
| | 300 | 81 | 82 |
| | 400 | 91 | 88 |
| D | 100 | 18 | 45 |
| (1st + 2nd surfactant, 1:1 ratio) | 200 | 63 | 74 |
| | 300 | 70 | 78 |
| | 400 | 77 | 84 |
| E | 100 | 25 | 42 |
| (1st + 2nd surfactant, 3:1 ratio) | 200 | 64 | 75 |
| | 300 | 74 | 78 |
| | 400 | 97 | 83 |

In the test of Example 1, Composition C–E of the invention, containing both a first and a second surfactant as herein defined, exhibited markedly enhanced herbicidal performance by comparison with either of Compositions A or B, each containing only one of the two surfactants but in the same total surfactant amount. The enhancement was especially pronounced on velvetleaf (ABUTH). This test provides clear evidence of a synergistic interaction between the first and second surfactant.

Example 2

Compositions A–E were tested on morningglory (*Ipomoea* sp., IPOSS) and prickly sida (*Sida spinosa*, SIDSP). Plants of IPOSS were sprayed 13 days and plants of SIDSP 25 days after planting. Evaluation of herbicial effectiveness was conducted 17 days after treatment (DAT). Results are shown in the following table.

| Composition | Glyphosate rate g a.e./ha | % Inhibition IPOSS | SIDSP |
|---|---|---|---|
| A | 200 | 33 | 10 |
| (2nd surfactant only) | 400 | 47 | 43 |
| | 600 | 52 | 50 |
| | 800 | 58 | 61 |
| B | 200 | 33 | 23 |
| (1st surfactant only) | 400 | 52 | 49 |
| | 600 | 53 | 62 |
| | 800 | 71 | 65 |
| C | 200 | 28 | 46 |
| (1st + 2nd surfactant, 1:3 ratio) | 400 | 53 | 65 |
| | 600 | 41 | 79 |
| | 800 | 78 | 85 |
| D | 200 | 20 | 30 |
| (1st + 2nd surfactant, 1:1 ratio) | 400 | 55 | 53 |
| | 600 | 40 | 65 |
| | 800 | 54 | 77 |
| E | 200 | 53 | 45 |
| (1st + 2nd surfactant, 3:1 ratio) | 400 | 42 | 70 |
| | 600 | 85 | 87 |
| | 800 | 88 | 90 |

In the test of Example 2, Compositions C–E the invention, containing both a first and a second surfactant as herein defined, again exhibited markedly enhanced herbicial performance by comparison with eithrer of Compositions A or B, each containing only one of the two surfactants but in the same total surfactant amount. The enhancements was especially pronounced on prickly sida (SIDSP). Data on morningglory (IPOSS) were more variable; the relatively poor performance of Composition D on IPOSS is out of line wit other results and is believed to be an artifact arising from this variation. This test provides further clear evidence of a synergistic interaction between the first and second surfactant.

The preceding description of specifics embodiments of the present invention is not intended to be a complete list of every possible embodiment of the invention. Persons skilled in this field will recognize that modifications can be made to the specific embodiments described herein that remain the scope of the invention.

What is claimed is:

1. A method of enhancing herbicidal activity of a glyphosate herbicide, comprising adding to said glyphosate herbicide a first surfactant and a second surfactant at a weight ratio of total surfactant to form a composition consisting essentially of glyphosate, a first surfactant, and a second surfactant to glyphosate acid equivalent of about 1.30 to about 2:1, wherein said first surfactant has a chemical structure comprising a cationic or protonatable amino group and a $C_{8-24}$ hydrocarbyl group, and said second surfactant has the chemical formula

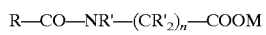

R—CO—NR'—(CR'$_2$)$_n$—COOM where R is a $C_{7-23}$ hydrocarbyl group, n is 1 to 4, M is hydrogen or a cationic counterion, and R' groups are each independently hydrogen, $C_{1-4}$ alkyl or a group —(CH$_2$)$_m$—COOM where m is 1 to 4 and M is as defined immediately above, with the proviso that no more than one R' group is such a group —(CH$_2$)$_m$—COOM and the weight ratio of said first surfactant to said second surfactant being about 1:10 to about 10:1.

2. The method of claim 1 wherein said first surfactant is selected from: a tertiary alkylamine and alkyletheramine; polyoxyethylene tertiary alkylamine and alkyletheramine; quaternary ammonium; pyridine; imidazoline; polyoxyethylene alkylamine and alkyletheramine oxide; an alkylbetaine; and alkyl diamine and a polyoxyethylene alkyl diamine.

3. The method of claim 1 wherein said first surfactant is a tertiary alkylamine or alkyletheramine surfactant having the chemical formula

where $R^1$ is a $C_{8-24}$ hydrocarbyl group, optionally interrupted by one or more ether linkages, and $R^2$ and $R^3$ are (a) independently $C_{1-4}$ alkyl groups, or (b) polyoxyalkylene chains having in total 2 to about 100 $C_{2-4}$ alkylene oxide units.

4. The method of claim 3 wherein $R^1$ is a $C_{12-18}$ hydrocarbyl group and $R^2$ and $R^3$ are polyoxyethylene chains having in total 2 to about 100 ethylene oxide units.

5. The method of claim 1 wherein, in the chemical formula for said second surfactant, the group R—CO— is a $C_{12-18}$ linear acyl moiety derived from one or more fatty acids.

6. The method of claim 1 wherein said second surfactant is an N—($C_{12-18}$ linear acyl) derivative of an α-amino acid.

7. The method of claim 6 wherein said α-amino acid is selected from alanine, aspartic acid, glutamic acid, glycine, isoleucine, leucine, sarcosine and valine.

8. The method of claim 6 wherein said α-amino acid is sarcosine.

9. The method of claim 1 wherein said first surfactant and said second surfactant are present in a weight ratio of about 1:5 to about 5:1.

10. The method of claim 1 wherein the weight ratio of total surfactant to glyphosate acid equivalent is about 1:10 to about 1:1.

11. The method of claim 1 wherein the weight ratio of total surfactant to glyphosate acid equivalent is about 1:6 to about 1:2.

12. The method of claim 1 wherein the glyphosate herbicide is a water-soluble salt of glyphosate with a monovalent counterion.

13. The method of claim 12 wherein the salt of glyphosate is selected from sodium, potassium, ammonium, $C_{1-16}$ organic ammonium and $C_{1-16}$ organic sulfonium salts.

14. The method of claim 12 wherein the salt of glyphosate is selected from sodium, potassium, ammonium, dimethylammonium, monoethanolammonium, n-propylammonium, isopropylammonium and trimethylsulfonium salts.

15. A herbicidal composition consisting essentially of (a) a glyphosate herbicide; (b) a first surfactant having a chemical structure comprising a cationic or protonatable amino group and a $C_{8-24}$ hydrocarbyl group,; and (c) a second surfactant having the chemical formula R—CO—NR'—(CR'$_2$)$_n$—COOM where R is a $C_{7-23}$ hydrocarbyl group, n is 1 to 4, M is hydrogen or a cationic counterion, and R' groups are each independently hydrogen, $C_{1-4}$ alkyl or a group —(CH$_2$)$_m$—COOM where m is 1 to 4 and M is as defined immediately above, with the proviso that no more than one $R^1$ group is such a group —(CH$_2$)$_m$—COOM; the weight ratio of said first surfactant to said second surfactant being about 1:10 to about 10:1, and the weight ratio of total surfactant to glyphosate acid equivalent being about 1:30 to about 2:1.

16. The composition of claim 15 wherein said first surfactant is selected from: a tertiary alkylamine and alkyletheramine; polyoxyethylene tertiary alkylamine and alkyletheramine; quaternary ammonium; pyridine; imidazoline; polyoxyethylene alkylamine and alkyletheramine oxide; an alkylbetaine; and alkyl diamine and a polyoxyethylene alkyl diamine.

17. The composition of claim 15 wherein said first surfactant is a tertiary alkylamine or alkyletheramine surfactant having the chemical formula

where $R^1$ is a $C_{8-24}$ hydrocarbyl group, optionally interrupted by one or more ether linkages, and $R^2$ and $R^3$ are (a) independently $C_{1-4}$ alkyl groups, or (b) polyoxyalkylene chains having in total 2 to about 100 $C_{2-4}$ alkylene oxide units.

18. The composition of claim 17 wherein $R^1$ is a $C_{12-18}$ hydrocarbyl group and $R^2$ and $R^3$ are polyoxyethylene chains having in total 2 to about 100 ethylene oxide units.

19. The composition of claim 15 wherein, in the chemical formula for said second surfactant, the group R—CO— is a $C_{12-18}$ linear acyl moiety derived from one or more fatty acids.

20. The composition of claim 15 wherein said second surfactant is an N—($C_{12-18}$ linear acyl) derivative of an α-amino acid.

21. The composition of claim 20 wherein said α-amino acid is selected from alanine, aspartic acid, glutamic acid, glycine, isoleucine, leucine, sarcosine and valine.

22. The composition of claim 20 wherein said α-amino acid is sarcosine.

23. The composition of claim 15 wherein said first surfactant and said second surfactant are present in a weight ratio of about 1:5 to about 5:1.

24. The composition of claim 15 wherein the weight ratio of total surfactant to glyphosate acid equivalent is about 1:10 to about 1:1.

25. The composition of claim 15 wherein the weight ratio of total surfactant to glyphosate acid equivalent is about 1:6 to about 1:2.

26. The composition of claim 15 wherein the glyphosate herbicide is a water-soluble salt of glyphosate with a monovalent counterion.

27. The composition of claim 26 wherein the salt of glyphosate is selected from sodium, potassium, ammonium, $C_{1-16}$ organic ammonium and $C_{1-16}$ organic sulfonium salts.

28. The composition of claim 26 wherein the salt of glyphosate is selected from sodium, potassium, ammonium, dimethylammonium, monoethanolammonium, n-propylammonium, isopropylammonium and trimethylsulfonium salts.

29. The composition of claim 15 that is a dilute aqueous plant treatment composition having a glyphosate acid equivalent content of about 0.1% to about 10% by weight.

30. The composition of claim 15 that is an aqueous concentrate composition having a glyphosate acid equivalent content of about 10% to about 50% by weight.

31. The composition of claim 15 that is a dry water-soluble or water-dispersible composition having a glyphosate acid equivalent content of about 5% to about 80% by weight.

32. A method of killing or controlling weeds comprising application to foliage of said weeds a composition of claim 29 in a volume of about 25 to about 1000 l/ha.

* * * * *

UNITED STATES PATENT AND TRADEMARK OFFICE
CERTIFICATE OF CORRECTION

PATENT NO. : 6,908,882 B1
DATED : June 21, 2005
INVENTOR(S) : David Z. Becher et al.

It is certified that error appears in the above-identified patent and that said Letters Patent is hereby corrected as shown below:

<u>Column 5,</u>
Line 44, "wilts" should read -- units --.
Line 64, "group 13" should read -- group-(CH2)m-COOM --.

<u>Column 12,</u>
Line 36, "wit" should read -- with --.
Lines 50-51, "surfactant at a weight ratio of total surfactant to form" should read -- surfactant to form --.
Line 53, "surfactant to" should read -- surfactant at a weight ratio of total surfactant to --; and "1.30" should read -- 1:30 --.

Signed and Sealed this

Twenty-eighth Day of March, 2006

JON W. DUDAS
*Director of the United States Patent and Trademark Office*